United States Patent [19]

Thoseby et al.

[11] Patent Number: 5,304,662

[45] Date of Patent: Apr. 19, 1994

[54] POLYGLYCIDYL COMPOUNDS

[75] Inventors: Michael R. Thoseby, Cambridge, England; Bryan Dobinson, Oberwil, Switzerland

[73] Assignee: Ciba-Geigy Corporation, Ardsley, N.Y.

[21] Appl. No.: 900

[22] Filed: Jan. 6, 1993

[30] Foreign Application Priority Data

Jan. 11, 1992 [GB] United Kingdom ............... 9200566

[51] Int. Cl.$^5$ ............... C07D 303/12; C07D 303/34; C08G 59/00
[52] U.S. Cl. ............... 549/556; 549/555; 549/560; 528/418
[58] Field of Search ............... 549/555, 548, 556, 560

[56] References Cited

U.S. PATENT DOCUMENTS 5,242,996  9/1993  Yamada et al. ............... 568/649

FOREIGN PATENT DOCUMENTS 1353663  5/1974  United Kingdom ............... 549/555

OTHER PUBLICATIONS

CA 116(16): 153083t Yamada et al., Modified epoxy resins . . . 1991.
CA 117(18): 172737w Yamada et al., Epoxy resins . . . 1992.

*Primary Examiner*—Joseph E. Evans
*Assistant Examiner*—Rebecca Cook
*Attorney, Agent, or Firm*—William A. Teoli, Jr.

[57] ABSTRACT

A compound having the formula (I):

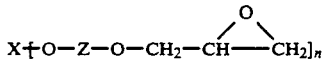

in which n is an integer ranging from 2 to 6; X is the residue of an optionally substituted primary or secondary aliphatic or cycloaliphatic polyol of formula II:

$$X(OH)_n \qquad \text{II}$$

in which X and n have their previous significance; and Z is a group of formula:

$$-CH_2-CH(CH_2OY)-$$

in which Y is the residue of an optionally substituted primary or secondary aliphatic or cycloaliphatic monohydric alcohol, or Z is a group of formula:

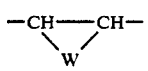

in which W is an optionally substituted aliphatic carbon chain, which may contain one or more heteroatoms, or Z is a group of formula $$-CH_2-CH(T)-$$

in which T is an aliphatic or cycloaliphatic alkyl group.

6 Claims, No Drawings

POLYGLYCIDYL COMPOUNDS

The present invention relates to new compounds, in particular to poly(glycidyl) ethers of aliphatic polyfunctional secondary alcohols; to the production of these compounds; and to their use.

In U.S. Pat. No. 4,284,574 there are disclosed poly(glycidyl) ethers of aromatic di-secondary alcohols having the formula:

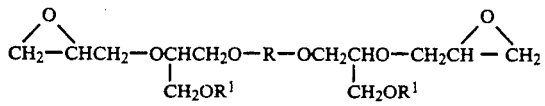

in which R is phenylene or naphthylene each optionally substituted by $C_1$-$C_4$ alkyl, chlorine or bromine, or a radical consisting of two or three phenylene groups linked by one or two carbon-carbon bonds, ether oxygen atoms, sulphur atoms, sulphonyl groups, sulphoxide groups, or $C_1$-$C_5$ alkylene groups, optionally substituted in one or two phenylene groups, by at most two $C_1$-$C_4$ alkyl group or chlorine or bromine atoms; and each $R^1$ is $C_1$-$C_{16}$ alkyl optionally substituted by at most four chlorine or bromine atoms, $C_2$-$C_6$ alkenyl optionally substituted by at most four chlorine or bromine atoms, phenyl or naphthyl optionally substituted by one or two chlorine or bromine atoms or $C_1$-$C_4$ alkyl groups, phenylalkyl or naphthylalkyl optionally substituted by one or two chlorine or bromine atoms or one or two $C_1$-$C_4$ alkyl groups, a mononuclear $C_3$-$C_6$ cycloalkyl group or a mononuclear $C_4$-$C_{10}$ cycloalkylalkyl group.

These compounds are generally of low viscosity, and are useful as casting resins.

We have now found certain new glycidyl compounds, derived from polyhydric aliphatic alcohols, which have lower viscosity, a better diluent effect and easier processability, relative to the compounds disclosed in U.S. Pat. No. 4,284,574.

Accordingly, the present invention provides compounds having the formula I:

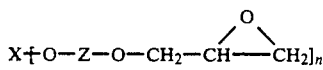

in which n is an integer ranging from 2 to 6; X is the residue of an optionally substituted primary or secondary aliphatic or cycloaliphatic polyol of formula $X(OH)_n$ (II) in which X and n have their previous significance; and Z is a group of formula:

—CH$_2$—CH(CH$_2$OY)— in which Y is the residue of an optionally substituted primary or secondary aliphatic or cycloaliphatic monohydric alcohol, or Z is a group of formula:

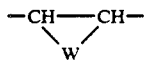

in which W is an optionally substituted aliphatic carbon chain which may contain one or more heteroatoms e.g. oxygen or sulphur atoms or Z is a group of formula —CH$_2$—CH—(T)— in which T is an aliphatic or cycloaliphatic alkyl group.

When X is a divalent residue, it is preferably, the residue of a straight- or branched-chain $C_1$-$C_8$ alkylene diol, or a $C_5$-$C_8$ cycloaliphatic diol, in which the ring may be optionally substituted, e.g. by one or more $C_1$-$C_4$ alkyl groups, or may be interrupted by O— or S— atoms or several cycloalkylene residues X may be bonded together, optionally via a bridge member. When X is a trivalent residue, or it has a higher valency, it preferably contains a $C_1$-$C_8$ aliphatic or $C_5$-$C_8$-cycloaliphatic structural element. The residue X may be substituted by functional groups, provided that such groups do not inactivate any Lewis acid catalysts used in the production of the compounds of formula I and do not undergo reaction with epichlorohydrin.

Specific examples of preferred aliphatic diols of formula II include diethylene glycol, triethylene glycol and higher polyoxyethylene glycols; propane-1,2-diol, propane-1,3-diol and higher polyoxypropylene glycols; neopentyl glycol; butane-1,4-diol and higher poly(oxytetramethylene) glycols; pentane-1,5-diol; hexane-1,6-diol; and octane-1,8-diol.

Examples of preferred aliphatic triols of formula II are 1,1,1-trimethylolpropane, glycerol, hexane-1,2,6-triol and 1,1,1-trimethylolethane. Other aliphatic triols of formula II which are commercially available and provide preferred residues X are adducts of simple polyols, such as glycerol, hexane-1,2,5-triol and hexane-2,4,6-triol, with propylene oxide and/or ethylene oxide.

Tetrafunctional aliphatic alcohols of formula II which are preferred include pentaerythritol and 3,3,7,7-tetra(hydroxymethyl)-5-oxanonane.

Preferred higher aliphatic poly-hydroxy compounds of formula II include dipentaerythritol, tripentaerythritol, mannitol, sorbitol, polyvinyl alcohol, partially hydrolyzed polyvinyl esters of acetals, and hydroxyalkyl acrylate, methacrylate or itaconate polymers and copolymers.

Preferred cycloaliphatic alcohols of formula II include resorcitol, quinitol, bis(4-hydroxycyclohexyl)methane, 2,2-bis(4-hydroxycyclohexyl) propane, cyclohexanedimethanol and 1,1-bis(hydroxymethyl)cyclohex-3-one.

Alcohols of formula II containing further functional groups which are preferred include polycaprolactone diols and polyols and derivatives of poly(epichlorohydrin).

When Z is a group —CH$_2$—CH (CH$_2$OY)—, Y is preferably the residue of an optionally substituted primary or secondary $C_1$-$C_8$ aliphatic monohydric alcohol or a $C_5$-$C_8$ cycloaliphatic monohydric alcohol, e.g. methanol, ethanol, propanol, isopropanol, n-butanol, n-hexanol, n-octanol or 2-ethylhexanol; or cyclopentanol, cyclohexanol, or cyclooctanol, especially a $C_1$-$C_8$ alkyl residue such as methyl, ethyl, propyl, n-butyl, 2-ethylhexyl or n-octyl group.

When Z is a group

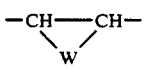

W is preferably a $C_3$-$C_6$ aliphatic carbon chain which may be optionally substituted by one or more $C_1$-$C_4$ alkyl groups.

When Z is a group —$CH_2CH(T)$—, wherein T is preferably a primary or secondary $C_1$-$C_8$ aliphatic alkyl group or cycloaliphatic alkyl group.

The compounds of formula I may be produced by reacting a compound having the formula III:

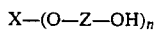

X—(O—Z—OH)$_n$     III in which n, X and Z have their previous significance, with epichlorohydrin, in the presence of an alkali and a phase transfer catalyst.

The polyol of formula III is preferably treated with at least 2.5, especially 3 to 8 molar equivalents of epichlorohydrin, in the presence of an alkali and a phase transfer catalyst. The alkali is preferably an alkali metal hydroxide, especially sodium hydroxide. The phase transfer catalyst is preferably a tetra-alkylammonium halide, e.g. methyltrioctylammonium chloride, methyltridecylammonium chloride benzyltrimethylammonium chloride or tetramethylammonium chloride, or a tertiary amine or quaternary ammonium base such as benzyltrimethylammonium hydroxide.

The reaction is preferably performed at an elevated temperature, especially at a temperature ranging from 40° to 100° C.

The starting materials of formula III are either known compounds, or they can be produced by methods which are well-known per se.

Thus, when Z is a group of formula —$CH_2$—CH ($CH_2OY$)—, the relevant compounds of formula III may be obtained by reacting a polyol of formula II with n moles of a compound having the formula IV:

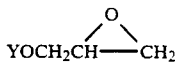

YOCH$_2$CH——CH$_2$     IV in which Y has its previous significance, in the presence of a Lewis acid catalyst such as boron trifluoride, or complexes thereof, stannic chloride, or a salt of trifluoromethanesulphonic acid or perchloric acid.

Alternatively, when Z is a group of formula:

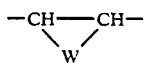

—CH——CH—
  \\ /
   W in which W has its previous significance, the relevant compounds of formula III may be obtained by reacting a polyol of formula II with n moles of a compound of formula V:

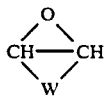

CH——CH
  \\ /
   W     V in which W has its previous significance, in the presence of a Lewis acid catalyst.

When Z is a group of formula —$CH_2CH(T)$—the relevant compounds of formula III may be obtained by reacting a polyol of formula II with a moles of a compound of formula VI:

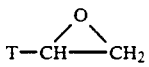

T—CH——CH$_2$     VI in which T has its previous significance, in the presence of a Lewis acid catalyst.

Preferred salts of trifluoromethanesulphonic acid and perchloric acid are those of zinc, cadmium, aluminium, cerium, yttrium, ytterbium, cobalt, iron and especially lanthanum.

The glycidyl compounds of formula I may be cured, with curing agents which are known for use in curing epoxide resins, to form insoluble, infusible products having valuable technical properties. Their low viscosity renders the glycidyl ethers of formula I eminently suitable for use as casting resins. They also find use, however, as laminating resins, surface coating resins, dipping resins, moulding compositions, potting and insulating compounds for the electrical industry, and in the manufacture of such products.

If desired, the glycidyl ethers of formula I may be cured in the presence of other epoxide resins.

Accordingly the present invention also provides a curable composition comprising a glycidyl compound of formula I and a curing agent for the compound of formula I.

As examples of curing agents may be mentioned aliphatic, cycloaliphatic, aromatic, and heterocyclic amines such as m- and p-phenylenediamine, bis(4-aminophenyl)methane, anilineformaldehyde resins, bis(4-aminophenyl) sulphone, ethylenediamine, propane-1,2-diamine, propane-1,3-diamine, N,N-diethylethylenediamine, hexamethylenediamine, diethylenetriamine, triethylenetetramine, tetraethylenepentamine, N-(2-hydroxyethyl)-, N-(2-hydroxypropyl)-, and N-(2-cyanoethyl)-diethylenetramine, 2,2,4-trimethylhexane-1,6-diamine, 2,3,3-trimethylhexane-1,6-diamine, m-xylylenediamine, N,N-dimethyl- and N,N-diethylpropane-1,3-diamine, ethanolamine, bis(4-aminocyclohexyl)methane, 2,2-bis(4-aminocyclohexyl)propane, 2,2-bis(4-amino-3-methylcyclohexyl)propane, 3-aminomethyl-3,5,5-trimethylcyclohexylamine (isophoronediamine), and N-(2-aminoethyl)piperazine; dicyandiamide; polyaminoamides, e.g. those prepared from aliphatic polyamines and dimerised or trimerised unsaturated fatty acids; adducts of amines with stoichiometric deficits of polyepoxides such as a diglycidyl ether; isocyanates and isothiocyanates; polyhydric phenols, e.g. resorcinol, hydroquinone, 2,2-bis(4-hydroxyphenyl)propane, phenol-aldehyde resins, and oil-modified phenol-aldehyde resins, phosphoric acid; polythiols such as the "Thiokols" ("Thiokol" is registered trade mark); and polycarboxylic acids and their anhydrides, e.g. phthalic anhydride, tetrahydrophthalic anhydride, methylendomethylenetetrahydrophthalic anhydride, nonenylsuccinic anhydride, dodecenylsuccinic anhydride, hexahydrophthalic anhydride, hexachloroendomethylenetetrahydrophthalic anhydride and endomethylenetetrahydrophthalic anhydride and their mixtures, maleic anhydride, succinic anhydride, pyromellitic acid dianhydride, benzophenone-3,3',4,4'-tetracarboxylic acid dianhydride, polysebacic anhydride, polyazelaic anhydride, the acids corresponding to the aforementioned anhydrides, and also isophthalic acid, terephthalic acid, citric acid, and mellitic acid. Particularly preferred polycarboxylic acid or anhydride curing agents are those which, in admixture if necessary, are liquid at temperatures below 60° C. There may also be used catalytic polymerising agents, such as tertiary amines (for example 2,4,6-tris(dimethylaminomethyl)-phenol and other Mannich bases, N-benzyldimethylamine, and triethanolamine); alkali metal alkoxides of alcohols (for example, the sodium alcoholate of 2,4-dihydroxy-3-hydroxymethylpentane), stannous salts of alkanoic acids (for example, stannous octanoate), Friedel-Crafts catalysts such as boron trifluoride and its complexes; and chelates formed by reaction of boron trifluoride with, e.g., 1,3-diketones.

In conjunction with the curing agents there may also be used appropriate accelerators. When poly(aminoamides), dicyandiamides, polythiols, or polycarboxylic acid anhydrides are employed for curing, tertiary amines or their salts, quaternary ammonium compounds, or alkali metal alkoxides can serve as accelerators. Examples of specific accelerators are N-benzyldimethylamine, 2,4,6-tris(dimethylaminomethyl)phenol, imidazoles, and triamylammonium phenoxide.

Other accelerators which may be used include metal nitrates, particularly magnesium nitrate and manganese nitrate, fluorinated and chlorinated carboxylic acids and their salts, such as magnesium trifluoroacetate, sodium trifluoroacetate, magnesium trichloroacetate, and sodium trichloroacetate, trifluoromethanesulphonic acid and its salts, such as the manganese, zinc, magnesium, nickel, and cobalt salts, and magnesium perchlorate and calcium perchlorate.

An effective amount of the curing agent is employed. The proportion will depend on the chemical nature of the curing agent and the properties sought of the curable composition and its cured product; the optimum proportion can readily be determined by methods familiar to those skilled in the art. By way of illustration, however, when the curing agent is an amine there will normally be used from about 0.75 to 1.25 amino-hydrogen equivalents of the amine per 1,2-epoxy equivalent of the epoxide resin. When polycarboxylic acids or their anhydrides are used, usually from about 0.4 to 1.1 carboxylic acid, or carboxylic acid anhydride, equivalents are taken per 1,2-epoxy equivalent, while, with polyhydric phenols about 0.75 to 1.25 phenolic hydroxy equivalents of the curing agent per 1,2-epoxy equivalent are employed. Generally, from 1 to 40 parts by weight of a catalytic polymerising agent are used per 100 parts by weight of the epoxide resin.

Curing can be carried out, depending on the nature of the curing agent, at room temperature (say, 18° to 25° C.) or at higher temperature (50° to 250° C., for example).

If desired, curing or hardening can be carried out in two stages, for example by interrupting the curing reaction or, if a curing agent requiring an elevated temperature for complete curing is used, by only partially curing at a lower temperature, to give a still fusible and soluble, curable precondensate or "B-stage" product, for use in making moulding powders, sinter-coating powders, or prepregs in a manner known per se.

As already indicated, the compounds of this invention may be used with conventional epoxide resins.

In the usual methods of manufacturing many epoxide resins, mixtures of compounds of differing molecular weight are obtained, these mixtures ordinarily containing a proportion of compounds whose epoxide groups have undergone partial hydrolysis or in which epoxidation has not proceeded to completion. The average number of 1,2-epoxide groups per molecule of an epoxide resin need not be at least 2 and need not be integral; it is generally a fractional number, but must in any case be greater than 1.0.

Of the epoxide resins which may be used in admixture with the glycidyl ethers of formula I the more suitable are those wherein the epoxide groups are also terminal, i.e. of formula

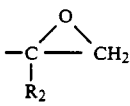

where $R^2$ denotes a hydrogen atom or a methyl group, and especially those where the groups are present as glycidyl or β-methylglycidyl groups directly attached to an atom of oxygen, nitrogen, or sulphur. Such resins include polyglycidyl and poly(β-methylglycidyl) esters obtainable by the reaction of a substance containing two or more carboxylic acid groups per molecule with epichlorohydrin, glycerol dichlorohydrin, or β-methylepichlorohydrin in the presence of alkali. The polyglycidyl esters may be derived from aliphatic carboxylic acids, e.g. oxalic acid, succinic acid, adipic acid, sebacic acid, or dimerised or trimerised linoleic acid, from cycloaliphatic carboxylic acids such as hexahydrophthalic, 4-methylhexahydrophthalic, tetrahydrophthalic, and 4-methyltetrahydrophthalic acid, or from aromatic carboxylic acids such as phthalic acid, isophthalic acid, and terephthalic acid.

Other epoxide resins which may be used include polyglycidyl and poly(β-methylglycidyl) ethers obtainable by the reaction of substances containing per molecule, two or more alcoholic hydroxy groups, or two or more phenolic hydroxy groups, with epichlorohydrin, glycerol dichlorohydrin, or β-methylepichlorohydrin, under alkaline conditions or, alternatively, in the presence of an acidic catalyst with subsequent treatment with alkali. Such polyglycidyl ethers may be derived from aliphatic alcohols, for example, ethylene glycol and poly(oxyethylene) glycols such as diethylene glycol and triethylene glycol, propylene glycol and poly(oxypropylene) glycols, propane-1,3-diol, butane-1,4-diol, pentane-1,5-diol, hexane-1,6-diol, hexane-2,4,6-triol, glycerol, 1,1,1-trimethylolpropane, and pentaerythritol; from cycloaliphatic alcohols, such as quinitol, 1,1-bis(-hydroxymethyl)cyclohex-3-ene, bis(4-hydroxycyclohexyl)methane, and 2,2-bis(4-hydroxycyclohexyl)propane, or from alcohols containing aromatic nuclei, such as N,N-bis(2-hydroxyethyl)aniline and 4,4'-bis(2-hydroxyethylamino)diphenylmethane. Preferably the polyglycidyl ethers are derived from substances containing two or more phenolic hydroxy groups per molecule, for example, resorcinol, catechol, hydroquinone, bis(4-hydroxyphenyl)methane, 1,1,2,2-tetrakis(4-hydroxyphenyl)methane, 4,4'-dihydroxydiphenyl, bis(4-hydroxyphenyl) sulphone, and especially, phenol-formaldehyde or cresol-formaldehyde novolac resins, 2,2-bis(4-hydroxyphenyl)propane (otherwise known as bisphenol A), and 2,2-bis(3,5-dibromo-4-hydroxyphenyl)-propane.

There may further be employed poly(N-glycidyl) compounds, such as are, for example, obtained by the dehydrochlorination of the reaction products of epichlorohydrin and amines containing at least two hydrogen atoms directly attached to nitrogen, such as aniline, n-butylamine, bis(4-aminophenyl)methane, bis(4-aminophenyl) sulphone, and bis(4-methylaminophenyl)methane. Other poly(N-glycidyl) compounds that may be used include triglycidyl isocyanurate, N,N'-diglycidyl derivatives of cyclic alkylene ureas such as ethyleneurea and 1,3-propyleneurea, and N,N'-diglycidyl derivatives of hydantoins such as 5,5-dimethylhydantoin.

Epoxide resins obtained by the epoxidation of cyclic and acyclic polyolefins may also be employed, such as vinylcyclohexene dioxide, limonene dioxide, dicyclopentadiene dioxide, 3,4-epoxydihydrodicyclopentadienyl glycidyl ether, the bis(3,4-epoxydihydrodicyclopentadienyl) ether of ethylene glycol, 3,4-epoxycyclohexylmethyl-3',4'-epoxycyclohexanecarboxylate and its 6,6'-dimethyl, derivative, the bis(3,4-epoxycyclohexanecarboxylate) of ethylene glycol, the acetal formed between 3,4-epoxycyclohexanecarboxyaldehyde and 1,1-bis(hydroxymethyl)-3, 4-epoxycyclohexane, bis(2,3-epoxycyclopentyl)ether, and epoxidized butadiene or copolymers of butadiene with ethylenic compounds such as styrene and vinyl acetate.

Especially suitable epoxide resins for mixing with the glycidyl ethers of formula I are polyglycidyl ethers of 2,2-bis(4-hydroxyphenyl)propane or a novalac from phenol (which may be substituted in the ring by a chlorine atom or an alkyl group of from 1 to 4 carbon atoms) and formaldehyde and having an epoxide content of at least 1.0 1,2-epoxide equivalent per kilogram.

The compositions of the invention may further contain plasticisers such as dibutyl phthalate, dioctyl phthalate, or tricresyl phosphate, inert diluents, and so-called reactive diluents, such as diglycidyl formal and especially monoepoxides such as butyl glycidyl ether, iso-octyl glycidyl ether, phenyl glycidyl ether, styrene oxide, glycidyl acrylate, glycidyl methacrylate, and glycidyl esters of synthetic, highly branched, predominantly tertiary, aliphatic monocarboxylic acids. They may also contain additives such as fillers, reinforcing materials, colouring matter, flow control agents, flame retardants, and mould lubricants. Suitable extenders, fillers, and reinforcing materials include asbestos, asphalt, bitumen, glass fibres, textile fibres, carbon fibres, boron fibres, mica, alumina, gypsum, titania, chalk, quartz flour, cellulose, kaolin, ground dolomite, wollastonite, collodial silica having a large specific surface such as that available under the registered trademark "Aerosil", clays modified by treatment with long chain amines (such as those available under the registered trade mark "Bentone"), powdered poly(vinyl chloride), powdered polyolefin hydrocarbons, powdered cured aminoplasts, and metal powders such as aluminium or iron powder. Flame retardants such as antimony trioxide may also be incorporated.

The following Examples illustrate the invention. Unless otherwise indicated, parts are by weight. Epoxide contents were determined by dissolving a sample in acetic acid and titrating against a standard solution of perchloric acid in acetic acid in the present of tetraethylammonium bromide, using crystal violet as indicator.

EXAMPLE 1

2,2-Bis(4-hydroxycyclohexyl)propane (100 g) is heated to 130° C. and a 25% solution of lanthanum triflate in 2-methoxyethanol (2.0 g) added. Butyl glycidyl ether (114.11 g) is added dropwise over 2 hrs and the reaction then maintained at 130° C. for a further 3 hrs, by which time the epoxide content of the reaction has fallen to zero.

100 Grams of this reaction product are mixed with epichlorohydrin (136.9 g) and 50% aqueous benzyltrimethylammonium chloride (2.0 g) and the reaction heated to 60° C. under a vacuum sufficient to cause reflux at 60° C. 50% Aqueous sodium hydroxide (37 g) is added over 2 hrs, water being azeotroped out under vacuum. At the end of the addition, azeotroping is continued for a further 90 mins, and then vacuum is broken. Water (80 ml) is added to dissolve the sodium chloride produced. The aqueous layer is discarded and the organic layer washed with 10% aqueous sodium dihydrogen phosphate (200 ml) and the solvent removed under reduced pressure to yield a yellow resin of epoxide content 2.60 mol/kg, total chlorine content 0.4% and viscosity at 25° C. 286 mPa.s.

EXAMPLE 2

2,2-Bis(4-hydroxycyclohexyl)propane (60.1 g) is heated to 130° C. and a 25% solution of zinc triflate in 2-methoxyethanol (3.0 g) added. Allyl glycidyl ether (57.0 g) is added dropwise over 2 hrs and the reaction then maintained at 130° C. for a further 90 mins, by which time the epoxide content of the reaction has fallen to zero.

90 Grams of this reaction product are mixed with epichlorohydrin (133.2 g) and 50% aqueous benzyltrimethylammonium chloride (1.8 g) and the reaction heated to 60° C. under a vacuum sufficient to cause reflux at 60° C. 50% Aqueous sodium hydroxide (31.7 g) is added over 2 hrs, water being azeotroped out under vacuum. At the end of the addition, azeotroping is continued for a further 90 mins, and vacuum is broken. Water (100 ml) is then added to dissolve the sodium chloride produced. The aqueous layer is discarded and the organic layer washed with 10% aqueous sodium dihydrogen phosphate (200 ml) and the solvent removed under reduced pressure to yield a yellow resin of epoxide content 2.44 mol/kg, total chlorine content 0.4% and viscosity at 25° C. 1014 mPa.s.

EXAMPLE 3

1,4-Cyclohexanedimethanol (72 g) is heated to 130° C. and a 25% solution of lanthanum triflate in 2-methoxyethanol (1.44 g) added. Butyl glycidyl ether (130.2 g) is added dropwise over 2 hrs and the reaction then maintained at 130° C. for a further 3 hrs, by which time the epoxide content of the reaction has fallen to zero.

100 Grams of this reaction product are mixed with epichlorohydrin (186.8 g) and 50% aqueous benzyltrimethylammonium chloride (3.0 g) and the reaction heated to 60° C. under a vacuum sufficient to cause reflux at 60° C. 50% Aqueous sodium hydroxide (50.5 g) is added over 2 hrs, water being azeotroped out under vacuum. At the end of the addition, azeotroping is continued for a further 90 mins, and then vacuum is broken. Water (106 ml) is added to dissolve the sodium chloride produced. The aqueous layer is discarded and the organic layer washed with 10% aqueous sodium dihydrogen phosphate (200 ml) and the solvent removed under reduced pressure to yield a pale yellow resin of epoxide content 4.04 mol/kg, total chlorine content 0.4% and viscosity at 25° C. 61 mPa.s.

EXAMPLE 4

1,1,1-Trimethylolpropane (67.09 g) is heated to 130° C. and a 25% solution of zinc triflate in 2-methoxyethanol (3.0 g) added. Butyl glycidyl ether (195.29 g) is added dropwise over 2 hrs and the reaction then maintained at 130° C. for a further 75 mins, by which time the epoxide content of the reaction has fallen to zero.

100 Grams of this reaction product are mixed with epichlorohydrin (226.5 g) and 50% aqueous benzyltrimethylammonium chloride (2.0 g) and the reaction heated to 60° C. under a vacuum sufficient to cause reflux at 60° C. 50% Aqueous sodium hydroxide (53.86 g) is added over 2 hrs, water being azeotroped out under vacuum. At the end of the addition, azeotroping is continued for a further 90 mins, and then vacuum is broken. Water (113 ml) is added to dissolve the sodium chloride produced. The aqueous layer is discarded and the organic layer washed with 10% aqueous sodium dihydrogen phosphate (200 ml) and the solvent removed under reduced pressure to yield a pale yellow resin of epoxide content 3.70 mol/kg, total chlorine content 0.27% and viscosity at 25° C. 52 mPa.s.

EXAMPLE 5

Sorbitol (40 g) is heated to 130° C. and a 25% solution of zinc triflate in 2-methoxyethanol (2.0 g) added. Butyl glycidyl ether (114.35 g) is then added dropwise over 2 hrs and the reaction then maintained at 130° C. for a further 4.5 hrs, by which time the epoxide content of the reaction has fallen to zero.

100 Grams of this reaction product are then mixed with epichlorohydrin (210.62 g) and 50% aqueous benzyltrimethylammonium chloride (3.0 g) and the reaction heated to 60° C. under a vacuum sufficient to cause reflux at 60° C. 50% Aqueous sodium hydroxide (50 g) is added over 2 hrs, water being azeotroped out under vacuum. At the end of the addition, azeotroping is continued for a further 90 mins, and vacuum is broken. Water (105 ml) is added to dissolve the sodium chloride produced. The aqueous layer is discarded and the organic layer washed with 10% aqueous sodium dihydrogen phosphate (200 ml) and the solvent removed under reduced pressure to yield a pale yellow resin of epoxide content 3.07 mol/kg, total chlorine content 0.34% and viscosity at 25° C. 490 mPa.s.

EXAMPLE 6

Sorbitol (40 g) is heated to 130° C. and a 25% solution of zinc triflate in 2-methoxyethanol (2.0 g) added. Butyl glycidyl ether (171.52 g) is added dropwise over 2 hrs and the reaction maintained at 130° C. for a further 90 mins, by which time the epoxide content of the reaction has fallen to zero.

100 Grams of this reaction product are mixed with epichlorohydrin (160.54 g) and 50% aqueous benzyltrimethylammonium chloride (2.0 g) and the reaction heated to 60° C. under a vacuum sufficient to cause reflux at 60° C. 50% Aqueous sodium hydroxide (50.86 g) is added over 2 hrs, water being azeotroped out under vacuum. At the end of the addition, azeotroping is continued for a further 90 mins, and then vacuum is broken. Water (107 ml) is added to dissolve the sodium chloride produced. The aqueous layer is discarded and the organic layer washed with 10% aqueous sodium hydrogen phosphate (200 ml) and the solvent removed under reduced pressure to yield a pale yellow resin of epoxide content 3.39 mol/kg, total chlorine content 0.28% and viscosity at 25° C. 580 mPa.s.

EXAMPLE 7

1,2,6-Hexanetriol (67.09 g) is heated to 130° C. and a 25% solution of zinc triflate in 2-methoxyethanol (3.0 g) added. Butyl glycidyl ether (195.29 g) is added dropwise over 2 hrs and the reaction then maintained at 130° C. for a further 3 hrs, by which time the epoxide content of the reaction has fallen to zero.

100 Grams of this reaction product are mixed with epichlorohydrin (215.41 g) and 50% aqueous benzyltrimethylammonium chloride (2.0 g) and the reaction heated to 60° C. under a vacuum sufficient to cause reflux at 60° C. 50% Aqueous sodium hydroxide (51.22 g) is added over 2 hrs, water being azeotroped out under vacuum. At the end of the addition, azeotroping is continued for a further 90 mins, and vacuum is broken. Water (108 ml) is added to dissolve the sodium chloride produced. The aqueous layer is discarded and the organic layer washed with 10% aqueous sodium dihydrogen phosphate (200 ml) and the solvent removed under reduced pressure to yield a yellow resin of epoxide content 3.57 mol/kg, total chlorine content 0.11% and viscosity at 25° C. 102 mPa.s.

EXAMPLE 8

A sample of resin produced according to Example 1 (10 g) is mixed with triethylenetetramine (6.33 g) and cast into a brass mould. It is left to cure for 16 hrs at room temperature, 6 hrs at 80° C., and 20 hrs at 100° C. The resulting material has a glass transition temperature of 29° C.

EXAMPLE 9

A sample of resin produced according to Example 1 (10 g) is mixed with methyltetrahydrophthalic anhydride (6.33 g) and N-methylimidazole (0.2 g) and cast into a brass mould. It is cured for 30 minutes at 100° C. and 7 hrs at 120° C. The resulting material has a glass transition temperature of 32° C.

EXAMPLE 10

A sample of resin produced according to Example 3 (10 g) is mixed with methyltetrahydrophthalic anhydride (6.49 g), and N-methylimidazole (0.2 g) and cast into a brass mould. It is cured for 30 minutes at 100° C. and 7 hrs at 120° C. The resulting material has a glass transition temperature of 19° C.

EXAMPLE 11

A sample of resin produced according to Example 4 (10 g) is mixed with methyltetrahydrophthalic anhydride (5.93 g), and N-methylimidazole (0.2 g) and cast into a brass mould. It is cured for 30 minutes at 100° C. and 7 hrs at 120° C. The resulting material has a glass transition temperature of 5° C.

EXAMPLE 12

A sample of resin produced according to Example 5 (10 g) is mixed with triethylenetetramine (6.37 g) and cast into a brass mould. It is left to cure for 16 hrs at room temperature, 6 hrs at 80° C., and 20 hrs at 100° C. The resulting material has a glass transition temperature of 4° C.

EXAMPLE 13

A sample of resin produced according to Example 5 (10 g) is mixed with methyltetrahydrophthalic anhydride (4.92 g), and N-methylimidazole (0.2 g) and cast into a brass mould. It is cured for 30 minutes at 100° C. and 7 hrs at 120° C. The resulting material has a glass transition temperature of 48° C.

EXAMPLE 14

A sample of resin produced according to Example 6 (10 g) is mixed with triethylenetetramine (7.03 g) and cast into a brass mould. It is left to cure for 16 hrs at room temperature, 6 hrs at 80° C., and 20 hrs at 100° C.

The resulting material has a glass transition temperature of −15° C.

EXAMPLE 15

A sample of resin produced according to Example 6 (10 g) is mixed with methyltetrahydrophthalic anhydride (5.44 g) and N-methylimidazole (0.2 g) and cast into a brass mould. It is cured for 30 minutes at 100° C. and 7 hrs at 120° C. The resulting material has a glass transition temperature of 44° C.

EXAMPLE 16

A sample of resin produced according to Example 7 (10 g) is mixed with triethylenetramine (7.403 g) and cast into a brass mould. It is left to cure for 16 hrs at room temperature, 6 hrs at 80° C., and 20 hrs at 100° C. The resulting material has a glass transition temperature of −17° C.

EXAMPLE 17

A sample of resin produced according to Example 7 (10 g) is mixed with methyltetrahydrophthalic anhydride (5.77 g), and N-methylimidazole (0.2 g) and cast into a brass mould. It is cured for 30 minutes at 100° C. and 7 hrs at 120° C. The resulting material has a glass transition temperature of 3° C.

We claim:

1. A compound having the formula (I):

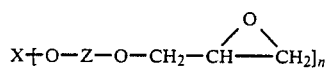

in which n is an integer ranging from 2 to 6; X is the residue of an optionally substituted primary or secondary aliphatic or cycloaliphatic polyol of formula II:

$$X(OH)_n \qquad II$$

in which X and n have their previous significance; and Z is a group of formula:

in which Y is the residue of an optionally substituted primary or secondary alkanol or cycloalkanol, or Z is a group of formula:

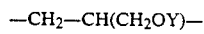

in which W is an optionally substituted aliphatic carbon chain which may contain one or more heteroatoms, or Z is a group of formula —CH$_2$—CH(T)— in which T is an aliphatic or cycloaliphatic residue.

2. A compound according to claim 1 in which X is a divalent residue of a C$_1$–C$_8$ alkylene diol or of a C$_5$–C$_8$ cycloaliphatic diol.

3. A compound according to claim 2 in which X is the residue of diethylene glycol, triethylene glycol or a higher polyoxyethylene glycol, propane-1,2-diol; propane-1,3-diol or a higher polyoxypropylene glycol; neopentyl glycol; butane-1,4-diol or a higher poly(oxytetramethylene)glycol; pentane-1,5-diol; hexane-1,5-diol; octane-1,8-diol; resorcitol; quinitol; bis(4-hydroxycyclohexyl)methane; 2,2-bis(4-hydroxycyclohexyl)-propane; cyclohexane dimethanol; or 1,1-bis(hydroxymethyl)cyclohex-3-one; 1,1,1-trimethylolpropane, glycerol, hexane-1,2,6-triol, 1,1,1-trimethylolethane and adducts of glycerol, hexane-1,2,5-triol or hexane-2,4,6-triol with propylene oxide and/or ethylene oxide; pentaerythritol or 3,3,7,7-tetra(hydroxymethyl),-5-oxanonane; dipentaerythritol, tripentaerythritol, mannitol, sorbitol, polyvinyl alcohol, partially hydrolyzed polyvinyl esters of acetals or hydroxyalkyl acrylate, methacrylate or itaconate polymers and copolymers; polycaprolactone diols or polyols or derivatives of poly(epichlorohydrin).

4. A compound according to claim 1 in which Z is a group —CH$_2$—CH (CH$_2$OY)— in which Y is the residue of an optionally substituted primary or secondary C$_1$–C$_8$ aliphatic monohydric alcohol or a C$_5$–C$_8$ cycloaliphatic monohydric alcohol.

5. A compound according to claim 1 in which Z is a group of formula

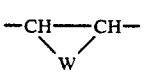

in which W is an optionally substituted C$_3$–C$_6$ aliphatic carbon chain.

6. A compound according to claim 1 in which Z is a group of formula —CH$_2$CH(T)— in which T is a C$_1$–C$_8$ primary or secondary aliphatic or cycloaliphatic alkyl residue.

* * * * *